United States Patent [19]

Davies

[11] 4,062,941

[45] Dec. 13, 1977

[54] METHOD FOR TREATING FUNGAL INFECTIONS USING CELL LYTIC ENZYMES

[75] Inventor: David Allen Lewis Davies, High Wycombe, England

[73] Assignee: G. D. Searle & Co. Ltd., High Wycombe, England

[21] Appl. No.: 689,700

[22] Filed: May 24, 1976

[30] Foreign Application Priority Data

June 11, 1975 United Kingdom .............. 25000/75

[51] Int. Cl.² .............................................. A61K 37/48
[52] U.S. Cl. .................................................... 424/94
[58] Field of Search ......................................... 424/94

[56] References Cited

PUBLICATIONS

Kawai – Chem. Abst. vol. 73, (1970), p. 73196K.

Primary Examiner—Sam Rosen
Attorney, Agent, or Firm—John J. McDonnell

[57] ABSTRACT

The present invention encompasses a method for treating fungal infections in animals comprising administering to animals in need of antifungal treatment an effective amount of fungal cell lytic enzymes extracted from Coprinus, Lycoperdon, or Bolbitius in conjunction with conventional antimycotic agents such as amphotericin B or Nystatin. The fungal cell lytic enzymes are extracted from Coprinus, Lycoperdon, and Bolbitius by conventional enzyme isolation techniques. These fungal cells lytic enzymes retain their activity in vivo, are relatively non toxic and destroy fungi by degrading fungal cell walls and weakening the fungal cell walls so that conventional antimycotic agents are far more effective. The method of the present invention is particularly useful in treating infections by opportunistic fungi such as *Aspergillus fumigatus* and *Candida albicans*.

6 Claims, No Drawings

METHOD FOR TREATING FUNGAL INFECTIONS USING CELL LYTIC ENZYMES

The present invention encompasses a method for treating fungal infections in animals comprising administering to animals in need of antifungal treatment an effective amount of fungal cell lytic anzymes extracted from Coprinus, Lycoperdon, or Bolbitius in conjunction with conventional antimycotic agents such as amphotericin B or Nystatin. The fungal cell lytic enzymes are extracted from Coprinus, Lycoperdon, and Bolbitius by conventional enzyme isolation techniques. The fungal cell lytic enzymes retain their activity in vivo, are relatively non toxic and destroy fungi by degrading fungal cell walls and weakening the fungal cell walls so that conventional antimy cotic agents are far more effective. The method of the present invention is particularly useful in treating infections by apportunistic fungi such as *Aspergillus fumigatus* and *Candida albicans.* The method of the present invention is also useful for treating *Trichophyton mentagrophytes* infections.

Fungal cell lytic enzymes are available from Lycoperdon, Coprinus, and Bolbitius. *Lycoperdon depressum, Lycoperdon gigantea,* and *Lycoperdon pyriforme* are preferred sources of fungal cell lytic anzymes. The specimens are collected in the field or cultured on solid or in liquid media.

Fresh, frozen or lyophilized whole specimens of Lycoperdon such as *L. pyriforme,* etc. are homogenized in water, saline, buffer or other suitable diluent. The homogenate is expressed through cloth and the resultant liquid centrifuged or filtered. The supernatant contains a crude enzyme mixture containing chitinase and various other enzymes. The crude extract is either stored at 4° C, lyophilized or purified as detailed below.

For enzyme production in culture, synthetic or natural media are used as long as essential nutrients are present. Such nutrients are well-known and include substances such as carbon source, a nitrogen source and inorganic compounds, etc., in appropriate amounts. Culturing of the organisms is carried out at a temperature of, for example, 20°–35° C and at a pH of, for example, 4–8 for a period of 2–15 days. In liquid media, culturing is carried out under aerobic conditions either by shaking or by stirring and aeration of the submerged culture. As a result, enzymes accumulate in both the culture medium and in the fungal mycelium.

Enzymes are extracted as follows: In the case of a solid medium, the mycelium and medium are homogenized and the resultant homogenate extracted with several volumes of water, saline, buffer or other suitable diluent. The resultant crude enzyme solutions are centrifuged or filtered in the liquid culture, the vegatative mycelium is separated from both by filtration or centrifugation. The filtrate or supernatant contains crude enzyme. A further crude enzyme solution is obtained by either homogenizing the vegetative mycelium immediately or by lyophilizing the mycelium and then homogenizing it in a suitable diluent. The resultant solution is filtered or centrifuged.

Enzyme solutions obtained by any of the above methods are purified and concentrated by one or more of the conventional enzyme-purifying methods such as precipitation by organic solvents, salting out, lyophilization, gel filtration and dialysis.

In a similar manner fungal cell lytic enzymes are prepared from Coprinus species such as *Coprinus comatus,* ATCC 12640 or ATCC 22314 or *Coprinus atramentarius* ATCC 22313\* or field harvested counterparts. Other Coprinus sources are listed on page 181 of ATCC Catalog of Strain, 11th ed. 12301 Parklawn Drive, Rockville, Maryland. Bolbitius species are sources of cell lytic enzymes and provide copious amounts of such enzymes.

\*Cultures are available to the public by writing American Type Culture Collection, 12301 Parklawn Drive, Rockville, Md.

The enzymes referred to are mixtures of chitinase, chitobiase, and $\alpha$ 1-3, $\alpha$ 1-6, $\beta$ 1-4 glucanases and $\beta$ 1-3 glucanase (laminarinase). Independent sources of laminarinase, chitinase and other carbohydrases are well known, Enzymes, Enzyme Handbook, Bartman Supp I, pp 312, Springe-Verlag, N.Y., N.Y., and references therein. However, no such enzyme or mixture of enzymes has previously been injected and shown to be of low toxicity and able to destroy fungal growths in vivo. Therefore, suitable sources of fungal cell lytic enzyme mixtures can be obtained from carefully selected sources - Coprinus, Lycoperdon, and Bolbitius.

Fungal cell lytic enzymes of the present invention are especially useful in combination with conventional antifungal agents such as nystatin, amphotericin-B, griseofulvin and other agents named in Chapter 12 of Cutting's Handbook of Pharmacology, 4th Edition, Appleton-Century-Crofts, N.Y., N.Y., pages 79-85.

Coprinus extracts have an $LD_{50}$ in mice of about 750 mg/kg and lycoperdon extracts have an $LD_{50}$ in mice of about 700 mg/kg. Effective amounts of the fungal cell lytic enzymes are about .5 mg/kg to 5 mg/kg of a purified preparation in a pharmaceutical carrier injected daily for two or three days. Dosage depends on purity of extracts from a particular species. Extracts of the present invention may be formulated in a variety of pharmaceutical carriers, buffers and emoluents.

A preferred embodiment of the present invention is the administration of fungal cell lytic enzymes in conjunction with drugs such as nystatin or amphotericin-B. Generally one regimen should follow the other with 24 hours. Those skilled in the pharmaceutical arts will recognize that the dose of fungal cell lytic enzymes and conventional antifungal agent will have to be varied to control stubborn fungal infections or to account for individual responsiveness.

U.S. Pat. No. 3,682,778 describes methods for extracting cell lytic enzymes from various Coprinus species. M. V. Tracey, Biochem Journal 61, 579-8(1955) discloses extracts of many Lycoperdon species and compares the chitinase activities of these extracts to chitinase activities of Coprinus extracts. Britich Patent Nos. 1,048,887 and 1,410,079 describe bacterial sources of cell lytic enzymes and their in vitro activity against pathogenic fungi and Kokai et al., Chem Abs 79, 133662V describes $\beta$-1-3-glucanase and chitinase as a fungicide for rice blight. Miura, Tohoku Journal of Exp. Med 59, No. 4 403(1954) indicates that in vitro activity of bacterial chitinase might suggest its use as a topical dermatomycosis agent. The method of the present invention is distinguished in that fungal cell lytic enzymes extracted from Coprinus, Lycoperdon, and Bolbitius in combination with antimycotic drugs such as amphotericin B or nystatin provide an effective treatment for fatal fungal infections. The enzymes have unexpectedly low toxicity.

The hereinafter set forth examples are intended to illustrate the invention and should not be construed as a limitation of the invention.

EXAMPLE 1

Toadstools of the Coprinus genus are collected when autolysis is just commencing, as shown by the darkening of the gills and the collection of dark fluid at the base. The collected toadstools are allowed to autolyse at 4° C for 36 hours and the fluid is then expressed through muslin. The resulting liquid, referred to as the "crude extract", is freeze dried.

A known amount of the crude extract is dissolved in water and centrifuged at 2,000 rpm for 10 minutes to remove insoluble material. The supernatant is separated on a Biogel P-200 (BioGel is trademark of Bio Rad Labs of Richmond, Calif.) column and fractions are collected. The fractions are monitored in a spectrophotometer at 280 nm for protein and tested for Chitinase activity and a variety of other carbohydrases by conventional specific assays, and using various accepted substrates, e.g. the non-specific substrate *Aspergillus fumigatus* mycelium (freeze dried) and specific substrates, for example, Chitin, Laminarin, Nigeran, Dextran, Cellulose, etc. The active fractions are pooled and freeze dried.

EXAMPLE 2

The activity of crude extracts of toadstools and commerical purified enzymes against fungal growth in vitro is shown below.

Mixtures of laminarinase and chitinase or crude extracts of *Coprinus comatus* (C.c.) and *Coprinus atramentarius* (C.a.) at levels of 0.25 mg/ml are added to freeze dried mycelium of *Aspergillus fumigatus*. The rate of Chitin degradation was measured by the method of Reissig, Strominger and Leloir, J. Biol. Chem. 1955, 219, 959–966.

|  |  | Chitin hydrolysed ($\mu$g/mg mycelium/hour) |
|---|---|---|
| Laminarinase & chitinase |  | 0.5 |
| Crude Extracts | C.a. | 1.2 |
|  | C.a. | 1.4 |
|  | C.a. + C.c. | 3.0 |

EXAMPLE 3

Preparations of enzymes and crude extracts are also tested against the growth of the fungus *Aspergillus fumigatus* in liquid culture. The reduction in growth of this fungus at 2 days when treated with different doses of enzymes of crude extracts are measured by the reduction in the dry weight of the mycellium.

|  |  | % weight reduction of *Aspergillus fumigatus* |
|---|---|---|
| Laminarinase & chitinase | (0.25 mg/ml) | 5% |
|  | (0.35 mg/ml) | 23% |
| Crude extract of C.c. | (0.25 mg/ml) | 22% |
|  | (0.35 mg/ml) | 64% |

EXAMPLE 4

It is shown that crude extracts of certain toadstools which contain chitinase in conjunction with certain other enzymes, are particularly potent against freeze dried mycelium and in reducing the growth of the fungus *Aspergillus fumigatus in vitro*. Combinations of purified enzymes are relatively poorly effective against such fungal growth in vitro.

The activity of such preparations against the lethal effects of *Aspergillus fumigatus* infection in mice is shown below. Mice are infected with approximately 5 $\times$ 10$^6$ spores of *Aspergillus fumigatus* and subsequently treated with various concentrations of purified enzymes or crude extracts of C.c. and C.a. The mean survival time of the mice is measured in days.

| Treatment |  | Mean survival (days) |
|---|---|---|
| None |  | 7 |
| Laminarinase and chitinase | 0.5 mg | 7 |
|  | 1.5 mg | 10 |
|  | 2.5 mg | 12 |
|  | 3 $\times$ 1.5 mg | 13 |
| Crude extract of C.c. & C.a. | 1.5 mg | 12 |
|  | 3 $\times$ 1.5 mg | Indefinite survival* |

*All mice survived 40 days and were sacrificed for autopsy.

EXAMPLE 5

The combined effect of enzyme compositions and drugs is enhanced by the sequential administration of these materials, particularly when the enzyme is given first followed by the drug.

Mice are challenged with approximately 5 $\times$ 10$^6$ spores of *Aspergillus fumigatus* injected intravenously. After one day the mice receive 1.5 mg of a mixture of crude extracts of C.c. and C.a. (enzymes) intraperitoneally and after two days an injection of one of the following drugs at the following doses, also intraperitoneally:

Amphotericin (0.6 $\mu$g), Griseofulvin (37.5 $\mu$g) and Nystatin (12.5 $\mu$g). The median time of death of the mice, in days, (the first day when 50% of the mice in each group are dead), is given below:

| Treatment | Mean survival (days) |
|---|---|
| None | 13.5 |
| Enzyme | 13.5 |
| Nystatin | 13.0 |
| Amphotericin | 13.5 |
| Griseofulvin | 14.0 |
| Enzyme + Nystatin | All alive at day 40 |
| Enzyme + Amphotericin | 75% alive at day 40 |
| Enzyme + Griseofulvin | 18.0 |

These results demonstrate the potent action of sequential administration of crude fungal extracts and drugs in protecting mice against the lethal effects of infection with *Aspergillus fumigatus*.

It has been shown that crude extracts of toadstools from the Coprinus genus are potent against chitin and against the growth of fungi in vitro. They are also capable of preventing the lethal effects of fungal infection in mice. Mixtures of enzymes available commercially, i.e., Chitinase and Laminarinase are relatively poorly effective compared even with the crude extracts described herein.

EXAMPLE 6

Fresh, frozen or lyophilized whole specimens of *Lycoperdon depressum* are homogenized in water, saline, buffer or other suitable diluent. The homogenate is expressed through cloth and the resultant liquid centrifuged or filtered. The supernatant contains crude enzyme mixture containing chitinase and other enzymes.

The activity of these extracts is illustrated by the following tests:

Mice are infected with $5 \times 10^6$ spores of *Aspergillus fumigatus* and subsequently treated with crude extracts from *Lycoperdon depressum*. The mean survival time of the mice is measured in days.

| Treatment | Mean survival (days) |
| --- | --- |
| None | 7 |
| 1.5 mg extract of *Lycoperdon depressum* | 10.8 |
| 3 × 1.5 mg extract of *Lycoperdon depressum* | All alive at day 45 |

EXAMPLE 7

Other experimental data exemplifying the methods of the present invention are summarized as follows:

Key to abbreviations used:
LC   commercially obtained laminarinase ($\beta$, 1-3 glucanase and chitinase in a 1:1 mixture.

CC   *Coprinus comatus* extract.
LD   *Lycoperdon depressum* extract    } crude extracts,
LP   *Lycoperdon pyriforme* extract    } except where stated
LP$_c$   *Lycoperdon pyriforme* culture extract AF   *Aspergillus fumigatus* (challenge dose $2 \times 10^6$ spores)
Calb   *Candida albicans* (challenge dose $2 \times 10^5$ cells)
TM   *Trichophyton mentagrophytes*
N =   Nystatin
A =   Amphotericin B
G =   Griseofulvin 1. Effect of enzyme levels and time of treatment on survival of mice with experimental AF infection.
   (a) Comparison of LC and CC enzymes administered after challenge (170 mice).
       Treatment regimes
       (a) single dose 5 hr or 24 hr after challenge.
       (b) Divided doses at 5, 29, 53 hr or 24, 48 & 72 hr after challenge.

| | AF | 1.5mg LC | 1.5mg CC | 3mg LC | 3mg CC | 2×1.5 mg LC | 2×1.5 mg CC | 4.5mg LC | 4.5mg CC | 3×1.5 mg LC | 3×1.5 mg CC | 3×3.3 mg N | 3×1.6 µg A | 3×10 mg G |
| --- | --- | --- | --- | --- | --- | --- | --- | --- | --- | --- | --- | --- | --- | --- |
| (a) | 14.7 | 14.9 | 16.1 | 14.5 | 17.5 | 16.8 | 21.0 | 12.5 | 23.1 | 23.6 | 37.1 | 23.4 | 17.6 | 15.1 |
| (b) | — | 17.5 | 21.0 | 18.2 | 32.5 | 28.0 | 41.3 | 12.3 | 56.1 | 26.3 | 100+ | 44.1 | 35.0 | 26.2 |

S.E. of means ± 3.65

Comments

1. Mixtures of Chitinase and Laminarinase ("LC") are too toxic for use (lethal dose about 14 mg/kg) and less effective than the products on which the claim is based (e.g. CC).

2. Divided doses (e.g. 3 × 1.5 mg CC per mouse) cures Aspergillus infection when appropriately administered and is more effective than this total amount given as a single dose.

c. Effect of treatment late in disease course (25 mice)

Mice are given a single treatment of either 4.5 mg, 3 mg or 1.5 mg CC 24 hr before their anticipated death i.e. 11 days after challenge.

Mean survival (days)

| | Mean survival (days) | | |
| --- | --- | --- | --- |
| AF | 1.5 mg | 3.0 mg | 4.5 mg |
| 14.1 | 19.4 | 19.6 | 35.6 |

S.E. of means ± 3.5

S.E. of means ± 3.5 d. Effect of CC extract and antimycotic drugs on survival of mice with experimental Aspergillus infection (see FIG. 4) (220 mice)

2 Levels of enzyme and drug are used in this experiment.

Level 1: Sub-curative giving only marginal increase in survival when given alone 24 hr after challenge.

Level 2: curative (in the case of CC extract) or maximum sub-toxic dose of drug. Program for enzyme + drug enzyme 24 hr after challenge — drug 48 hr after challenge

| | Mean survival (days) | | | |
| --- | --- | --- | --- | --- |
| AF | 1.5 mg CC | 12.5 µg N | 0.6 µg A | 37.5 µg G |
| 13.8 | 15.4 | 15.6 | 16.3 | 14.5 |
| | 3×1.5 mg CC | 3×3.3 mg N | 3×1.6 µg A | 3×100 mg G |
| | 150.0* | 30.6 | 23.2 | 21.0 |
| | 1.5mg CC/12.5µg N | 1.5mg CC/0.6µg A | | 1.5mg CC/37.5µg G |
| | 40.0 | 150.0* | | 19.0 |

S.E. means ± 5.0
*All mice still alive at 150 days

Comments

1. In all cases synergy occurred between drugs and enzymes at low levels.

2. Whith amphotericin + enzyme, mice are completely cured while highest permissible sub-toxic doses of amphotericin alone are only moderately effective in prolonging life.

3. *Lycoperdon depressum* and *L. pyriforme* extracts from fresh material and culture provide similar results.

e. Effect of CC on Aspergillus infections in mice receiving ALS before challenge. (35 mice).

Treatment programs were as follows:
1. ALS 300 ul 24 hr before AF challenge/saline
2. ALS/AF/3 × 1.5 mg CC at 24 hr intervals after challenge 3. ALS/AF/5 × 1.5 mg CC at 24 hr intervals after challenge
4. ALS/AF/1.5 mg CC/0.6 μg Amphotericin "
5. ALS/AF/1.5 mg CC/0.6 μg A/1.5 mg CC/0.6 μg A
6. ALS/AF/1.5 mg CC/saline/1.5 mg CC/saline
7. ALS/AF/saline/0.6 μg A/saline/0.6 μg A

| Treatment | Mean survival (days) | | | | | | |
|---|---|---|---|---|---|---|---|
| | 1 | 2 | 3 | 4 | 5 | 6 | 7 |
| | 8.6 | 25.6 | 39.6 | 24.0 | 50.0* | 15.0 | 8.6 |

S.E. of means ± 1.2
*All mice alive at 50 days

Alternate enzyme/drug injections at levels which have little effect on survival when administered alone are most effective in increasing survival f. Effect of enzymes on the course of disease in mice infected with C. albicans (25 mice)

Mice were infected intravenously with 2 × 10⁵ cells of *C. albicans* and treated with enzymes alone or with drug supplement as follows:

1. C. albicans challenge/saline
2. C. albicans/3 × 1.5 mg CC at 24 hr intervals after challenge
3. C. albicans/5 × 1.5 mg CC at 24 hr intervals after challenge
4. C. albicans/1.5 mg CC/0.6 μg Amphotericin
5. C. albicans/1.5 mg CC/0.6 μg A/1.5 mg CC/0.6 μg A
6. C. albicans/1.5 mg CC/saline/1.5 mg CC/saline
7. C. albicans/saline/0.6 μg A/saline/0.6 μg A

| Treatment | Mean survival (days) | | | | | | |
|---|---|---|---|---|---|---|---|
| | 1 | 2 | 3 | 4 | 5 | 6 | 7 |
| | 8.8 | 24.2 | 50.0* | 24.2 | 50.0* | 12.6 | 8.2 |

S.E. of means ± 2.8
*All mice alive at 50 days

Comments

1. Treatments 2 and 4 which cure mice with AF infections also prolong mean survival of Candida infected animals to 23.2 and 22 days, respectively.
2. Increasing the enzyme dose or alternating drug and enzyme markedly prolongs survival.

g. Effect of enzymes on superficial mycotic infections in guinea pigs

The shaved backs of Duncan Hartley guinea pigs are inoculated with *Trichophyton mentagrophytes*, a common dermatophyte. When infection is established (about 5 days) treatment is initiated, using enzymes in various concentrations and in different vehicles. The course of infection is followed by culturing samples of skin and hair taken from around the infected site before, during and after completion of treatment. Each animal receives a single daily treatment of approximately 0.5 g vehicle + enzyme.

| 1. 5% Polyvinyl alcohol base — enzyme concn. 4% w/v | | | | |
|---|---|---|---|---|
| | Mean % positive cultures | | | |
| | Before Treatment | After 4 treatments | After 8 treatments | 4 days after last treatment | 10 days after last treatment |
| PVA only | 100 | 80 | 100 | 100 | 100 |
| + 4% CC | 100 | 20 | 0 | 0 | 20 (relapse) |
| S.E. of means ± 6.82 | | | S.E. of means ± 7.1 | |

| | 2. Carbopol base | | | | | | | | | | | | | | |
|---|---|---|---|---|---|---|---|---|---|---|---|---|---|---|---|
| | Mean % positive Scrapes | | | | | % Positive Animals | | | | | Mean No. of Positive Colonies/Animal | | | | |
| | (a) | (b) | (c) | (d) | (e) | (a) | (b) | (c) | (d) | (e) | (a) | (b) | (c) | (d) | (e) |
| Carbopol only | 100 | 80 | 100 | 98.2 | 100 | 100 | 100 | 100 | 100 | 100 | 17.3 | 20.1 | 15.0 | 10.0 | 12.0 |
| +5% CC | 100 | 23 | 0 | 0 | 0 | 100 | 50 | 0 | 0 | 0 | 18.0 | 2.3 | 0 | 0 | 0 |
| +1% CC | 100 | 60 | x | 50 | 50 | 100 | 100 | x | 80 | 80 | 19.0 | 18.4 | x | 11.0 | 10.0 |
| +0.1% A | 100 | 60 | x | 80 | 80 | 100 | 100 | x | 100 | 100 | 18.3 | 19.1 | x | 10.5 | 10.0 |
| 1% CC + 0.1% A | 100 | 33.3 | x | 50 | 50 | 100 | 65 | x | 50 | 50 | 17.5 | 9.0 | x | 5.0 | 4.0 |
| S.E. of means ± | | 7.81 | — | 8.3 | 7.5 | | | | | | 4.6 | 3.41 | — | 3.9 | 4.1 |

(a) Before treatment
(b) After 4 treatments
(c) after 8 treatments
(d) 4 days after treatment ended
(e) 10 days after treatment ended
x - heavy contamination made counting of colonies impossible.

5% w/w/CC in Carbopol proves effective in clearing infection after 8 treatments. The amount of inoculum (expressed as no. of colonies/animal) is significantly reduced after only 4 treatments.

h. Effect of simultaneous administration of Amphotericin B and enzyme mixture on the course of experimental Aspergillus infections in mice. Treatments as follows:

1. AF challenge/saline at 24 and 48 hr after challenge
2. AF/1.5 mg CC at 24 hr/saline at 48 hr after challenge
3. AF/1.5 mg CC at 24 hr/1.5 mg CC at 48 hr
4. AF/0.6 μg Amphotericin at 24 hr/saline at 48 hr
5. AF/0.6 μg Amphotericin at 24 hr/0.6 μg at 48 hr
6. AF/1.5 mg CC + 0.6 μg A at 24 hr/saline at 48 hr
7. AF/1.5 mg CC + 0.6 μg A at 24 hr/1.5 mg CC + 0.6 μg A at 48 hr
8. AF/1.5 mg heat-inactivated CC + 0.6 μg A at 24 hr/1.5 mg HICC + 0.6 μg A at 48 hr

| Treatment | Mean survival (days) | | | | | | | |
|---|---|---|---|---|---|---|---|---|
| | 1 | 2 | 3 | 4 | 5 | 6 | 7 | 8 |
| | 13.9 | 25.1 | 50.3 | 16.1 | 23.1 | 51.4 | 90* | 24.2 |

S.E. of means ± 4.3
*All mice still alive at day 90
Note: Heat-inactivated enzyme has no synergy with drug

What is claimed is:
1. A method for treating fungal infections in animals comprising administering to an animal in need of anti- fungal treatment an effective amount of fungal cell lytic enzymes extracted from Coprinus or Lycoperdon.

2. A method for treating fungal infections in animals comprising administering to an animal in need of antifungal treatment an effective amount of fungal cell lytic enzymes extracted from Coprinus or Lycoperdon in conjunction with an antimycotic agent.

3. A method according to claim 2 for treating fungal infections in animals comprising administering to an animal in need of antifungal treatment an effective amount of fungal cell lytic enzymes extracted from Coprinus or Lycoperdon in conjunction with amphotericin-B or nystatin.

4. A method according to claim 2 wherein the fungal cell lytic enzyme is extracted from *Lycoperdon pyriforme*.

5. A method according to claim 2 wherein the fungal cell lytic enzyme is extracted from *Coprinus comatus*.

6. In a method for treating fungal infections by the administration of nystatin, amphotericin-B, or griseofulvin as antifungal agents, the improvement of which comprises the administration of effective amounts of fungal cell lytic anzymes extracted from Coprinus or Lycoperdon in conjunction with the antifungal agent.

* * * * *